United States Patent

Plant Pat. 3,828

Patented Feb. 3, 1976

3,828

CANADA BLUEGRASS PLANT

Arden Wayne Jacklin, Spokane, Wash., assignor to The Vaughan-Jacklin Corporation, Spokane, Wash.

Filed Oct. 17, 1974, Ser. No. 515,597

Int. Cl. A01h *5/12*

U.S. Cl. Plt.—88 1 Claim

ABSTRACT OF THE DISCLOSURE

A Canada bluegrass plant, which I have designated "Reubens," and which exhibits greatly improved seed producing capability, earlier maturity, and excellent adaptation to extremely poor growing conditions. This new variety has improved regrowth vigor and density when maintained under semi-turf conditions where occasional mowing is required.

This invention relates to a new and distinct variety of Canada bluegrass plant (*Poa compressa* L.), the novel characteristics of which reside particularly in its improved seed producing properties, earlier maturity, and excellent seed producing properties, earlier maturity, and excellent adaptation to poor growing conditions (including low moisture, low fertility, and low maintenance practices), producing a sod with greater density and regrowth vigor than common Canada bluegrass. The plant exhibits a high degree of apomixism and therefore reproduces asexually by means of disseminules through agamospermy. The plant has been asexually reproduced by means other than true seeds.

Discovery of the new variety occurred in 1970 when seed from a cultivated field of Canada bluegrass, near Reubens, Idaho, was planted for observation. In the ensuing years, plants of his new variety exhibited characteristics superior to those of common Canada bluegrass. Seed from selected mother plants was planted in rows and carefully rogued. Breeder seed from these mother plants was hand harvested, to be used for future seed increase.

A primary object of the invention is to provide a new and distinct Canada bluegrass plant having the improved characteristics referred to above and to be described in detail below.

Other objects and advantages of the invention will become more apparent from the following detailed description when taken in conjunction with the accompanying illustrations, in which.

Figure 1:
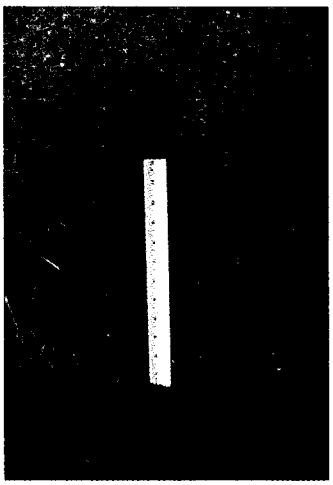
FIG. 1 is a color photograph showing a field of the new variety approximately one week before the initiation of anthesis.
Figure 2:
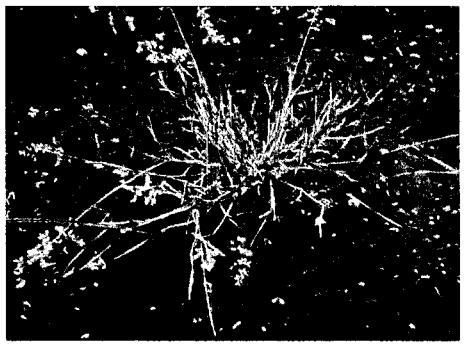
FIG. 2 is a color photograph showing the new variety growing in a spaced planting at approximately the same stage of development.
Figure 3:
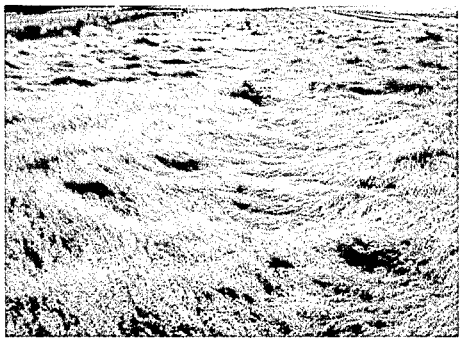
FIG. 3 is a color photograph showing the unique rust pigmentation at maturity of the new variety on the left and the green pigmentation of immature common Canada bluegrass on the right. Note the tendency of common Canada bluegrass to lodge.
Figure 4:
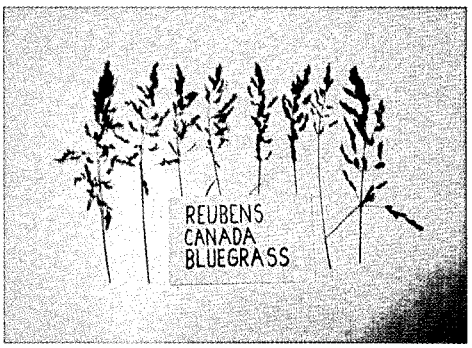
FIG. 4 is a black-and-white photograph showing randomly selected panicles of the new variety (Reubens)
Figure 5:
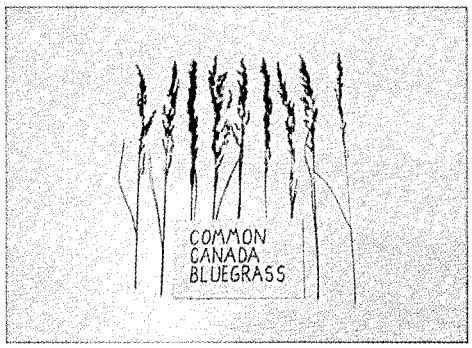
FIG. 5 is a black-and-white photograph showing randomly selected panicles of common Canada bluegrass.

The new variety possesses at least the following unique combination of characteristics:

(1) improved regrowth vigor and density when maintained under semi-turf conditions where occasional mowing is required.

(2) good rhizome and tiller development, producing a stand of excellent density and moderate horizontal spreading ability. An increased number of tillers produces a tighter sod than common Canada bluegrass.

(3) an attractive dark green color in spring when the plant is vegetative as opposed to the blue-green leaf color of common Canada bluegrass at the same time and location. Purple coloring appears on lower leaf sheaths when the plant is grown in locations where frost occurs. The dark green color of the new variety gives way to a blue-green color in late spring and then to its unique maturity pigmentation, light yellow-green stems and rust colored inflorescence.

(4) Excellent seed yielding potential coupled with earlier maturity and larger seed than that of common Canada bluegrass.

PLANT DESCRIPTION

Plants of the new variety and of common Canada bluegrass were grown in adjacent locations in Idaho under grass seed production conditions, for comparison purposes.

Leaves of the new variety remain a dark green color considerably after common Canada bluegrass leaves have taken on the species' characteristic blue-green color. Blades of the new variety are short, stiff, more numerous and narrower than common Canada bluegrass, with each side tapering to a boat-shaped apex. The blade is flat or slightly V-shaped, and prominent midvein is flanked on either side by longitudinally-oriented translucent lines. Leaves are folded in the bud. Ligule is membranous, short (0.2 to 1.2 mm., average 0.6), abrupt, commonly with a serrated leading edge, and more conspicuous than that of Kentucky bluegrass (*Poa pratensis* L). The collar is narrow, glabrous, and divided by a strong midvein. Auricles are absent. Sheaths are strongly compressed, sharply keeled, glabrous, split, flattened, more commonly tinged with purple pigmentation than common Canada bluegrass when grown under similar conditions. Plants resemble Kentucky bluegrass in having creeping rhizomes, but are easily recognized by the obscure side nerves of the lemmas and by their distinctly flattened culms.

Culms of the new variety mature as much as one week sooner than those of common Canada bluegrass when grown at the same location and under the same conditions. At maturity, they are profuse in number, flattened, with stiff, yellow-green stems, averaging 51 cm. in height when grown under post-harvest burn conditions and 43 cm. in height when harvest residue burning is not employed as a cultural practice of seed production. Conversely, mature culms of common Canada bluegrass have flattened, medium green stems with a moderate tendency toward lodging, average 61 cm. in height when burning is employed, and 53 cm. in height in natural unburned conditions. Common Canada bluegrass culms are solitary or few together, wiry, decumbent at base, with a close, narrow inflorescence and crowded spikelets.

The inflorescence of the new variety averages 7.4 cm. long and is a pyramidal open panicle with an erect main axis. The lower branches are usually in clusters of three, angular, slightly rough, with spikelets to the base of the branches, or the longer ones bare there. The inflorescence of the new variety is, at maturity, strongly red-brown in color, as opposed to the medium-green color of the still immature inflorescence of common Canada bluegrass. Spikelets are ovate, compressed, 3.1 to 6.0 mm. long (avg. 4.6), 3–6 flowered, anthers 1.3–1.5 mm. long, breaking up at maturity beneath each lemma. Glumes are persistent, ovate, oblong or elliptic, pointed, equal or slightly unequal, firm except for membranous margins, 3-nerved, and rough on the keels. Seed (disseminules) of the new variety are larger (2.0–2.8 mm., avg. 2.4) than that of common Canada bluegrass (1.6–

2.3 mm., avg. 2.1), light straw colored, and with intermediate nerves lacking. Lemmas overlap at first, later the margins inflex, narrowly oblong and blunt in side view, firm except for the membranous tips, obscurely 5-nerved, softly hairy on the keel and marginal nerves below the middle. Paleas about as long as lemmas, with two rough keels. The grain is tightly enclosed by the hardened lemma and palea.

Anthesis of the new variety occurs several weeks later than Kentucky bluegrass and 3–7 days earlier than common Canada bluegrass in the same locality.

Since soil and climatic factors influence morphological characteristics to some degree, these characters may vary slightly under different conditions, but the primary differences between the new variety and common Canada bluegrass remain unchanged. The morphological characteristics of Reubens and common Canada bluegrasses measured in 1974 at Spokane, Wash., are shown in Table 1, below:

TABLE 1.—MORPHOLOGICAL COMPARISONS

| | Average mature plant ht. (cm.) | | Avg. leaf width (mm.) | Average flag leaf angle from vertical (degrees) | Inflorescence description | | | | Avg. spikelet length (mm.) | Avg. seed size (mm.) | Avg. No. of branches at lowest node of inflorescence |
|---|---|---|---|---|---|---|---|---|---|---|---|
| | Burned [1] | Unburned [2] | | | Avg. length (cm.) | Avg. wt. (mg.) | Shape | Posture | | | |
| New variety | 51 | 43 | 3.9 | 40-45 | 5.5 | 43.7 | Open | Erect | 4.6 | 2.4 | 3.4 |
| Common Canada bluegrass | 61 | 53 | 4.4 | 10-30 | 8.6 | 71.6 | Compressed | Nodding | 3.4 | 2.1 | 2.2 |

[1] Burned=Stubble remaining after 1973 harvest was burned on the field. New growth emerged from underground crowns.
[2] Unburned=Stubble remaining from 1973 harvest was allowed to remain after straw was baled and removed.

Seed yield potential is indicated in Table 2, below, by a 1972 through 1974 comparison of the new variety and common Canada bluegrass to that of several Kentucky bluegrasses:

TABLE 2.—RESULTS OF IDAHO SEED YIELD TRIALS

| | Yield (kilograms per hectare) | | | | | |
|---|---|---|---|---|---|---|
| | Burned [1] | | | Unburned [2] | | |
| | 1972 | 1973 | 1974 | 1972 | 1973 | 1974 |
| New variety Canada bluegrass. | (3) | 1,391 | 1,224 | 988 | 961 | 784 |
| Common Canada bluegrass | (3) | 663 | 612 | 615 | 667 | 555 |
| Newport Kentucky bluegrass | (3) | 1,159 | 1,473 | 1,330 | 997 | 765 |
| Park Kentucky bluegrass | (3) | 1,058 | 612 | 1,085 | 650 | 701 |
| Kenblue Kentucky bluegrass | (3) | 1,600 | 999 | 885 | 973 | 669 |

[1] Burned=Stubble remaining after 1973 harvest was burned on the field. New growth emerged from underground crowns.
[2] Unburned=Stubble remaining from 1973 harvest was allowed to remain after straw was baled and removed.
[3] Because 1972 was the seedling or first year's harvest, burning was not employed. The burn following the 1973 harvest was the first burn treatment imposed.

AREAS OF PROBABLE ADAPTATION

Canada bluegrass is found in association with Kentucky bluegrass, but is only dominant on soils that are too acid, droughty, or deficient in nutrients for good growth of Kentucky bluegrass. It is excellent for soil conservation revegetation of disturbed areas where subsoil has been exposed. Best adapted to all cool season areas of Canada and the United States, Canada bluegrass will survive extremes of cold or dry conditions. While not recommended for lawns, Canada bluegrass, including the new variety, may be useful in roadside, mine tailing, and other turfgrass plantings on soils that are too dry or infertile for Kentucky Bluegrass. Value for turf use when compared to Kentucky bluegrass is limited mainly by open nature of sod formed, and by poor recovery after mowing.

REPRODUCTION AND PROPAGATION

Asexual reproduction of the new variety by disseminules (modified caryopses produced by agamospermy) has consistently produced progeny indistinguishable from the mother plant. The new variety cannot be sexually reproduced; i.e., it cannot be reproduced by true seeds.

The new variety has demonstrated excellent seed producing properties. In addition, it exhibits an attractive dark green to blue-green color and excellent persistence under extremely poor growing conditions.

What is claimed is:

1. A new and distinct variety of Canada bluegrass plant, substantially as herein shown and described, and characterized by and distinguished from common Canada bluegrass particularly by its greater seed yielding capability, earlier anthesis and disseminule maturity, reduced growth habit, stiff yellow-green stem and rust colored inflorescence at its maturity, while common Canada bluegrass is still immature, and an inflorescence which is a pyramidal open panicle with main axis moderately erect.

No references cited.

ROBERT E. BAGWILL, Primary Examiner

UNITED STATES PATENT OFFICE

CERTIFICATE OF CORRECTION

PATENT NO. : Plant Patent No. 3828

DATED : February 3, 1976

INVENTOR(S) : Arden Wayne Jacklin

It is certified that error appears in the above-identified patent and that said Letters Patent are hereby corrected as shown below:

Column 1, lines 24-25, cancel "and excellent seed producing properties, earlier maturity".

Column 1, line 37, change "his" to -- this --.

Signed and Sealed this

*twenty-fifth* Day of *May 1976*

[SEAL]

*Attest:*

RUTH C. MASON
*Attesting Officer*

C. MARSHALL DANN
*Commissioner of Patents and Trademarks*